US009456924B2

United States Patent
Noroozi et al.

(10) Patent No.: US 9,456,924 B2
(45) Date of Patent: Oct. 4, 2016

(54) VALVE POSITION DETECTION

(71) Applicant: Novartis AG, Basel (CH)

(72) Inventors: Zahra Noroozi, Aliso Viejo, CA (US); Ray Karam, Santa Barbara, CA (US); Nicholas M. Gunn, Newport Beach, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/257,235

(22) Filed: Apr. 21, 2014

(65) Prior Publication Data

US 2015/0297341 A1 Oct. 22, 2015

(51) Int. Cl.
*A61F 2/14* (2006.01)
*A61F 9/00* (2006.01)
*A61F 9/007* (2006.01)
*F16K 99/00* (2006.01)

(52) U.S. Cl.
CPC ....... *A61F 9/00781* (2013.01); *F16K 99/0015* (2013.01); *F16K 99/0048* (2013.01); *F16K 2099/0088* (2013.01)

(58) Field of Classification Search
CPC .......... A61F 9/00781; A61F 2250/0008; A61F 2250/0013; A61F 2250/0069; A61M 27/002; A61M 2205/0216; A61M 2205/0227; A61M 2205/0233; A61M 2205/0244; A61M 2205/0294; A61M 2205/04; A61M 2205/33; A61M 2205/3331; A61M 2205/3327; A61M 2205/3334; A61M 2205/3337; A61M 2205/3344
See application file for complete search history.

(56) References Cited

U.S. PATENT DOCUMENTS

| | | | | |
|---|---|---|---|---|
| 4,928,690 A | * | 5/1990 | Heilman | A61N 1/39 600/509 |
| 5,069,067 A | * | 12/1991 | Ingman | G01F 3/24 73/269 |
| 6,280,148 B1 | * | 8/2001 | Zengerle | H01L 41/00 417/212 |
| 8,257,295 B2 | * | 9/2012 | Rickard | A61B 3/16 604/8 |
| 2004/0127843 A1 | * | 7/2004 | Tu | A61F 9/0017 604/27 |
| 2005/0049578 A1 | * | 3/2005 | Tu | A61B 3/16 604/890.1 |
| 2005/0103114 A1 | * | 5/2005 | Bly | G01L 9/0042 73/754 |
| 2007/0089516 A1 | * | 4/2007 | Khuri-Yakub | G01N 27/221 73/579 |
| 2010/0042209 A1 | * | 2/2010 | Guarnieri | A61F 9/00781 623/4.1 |
| 2012/0296258 A1 | * | 11/2012 | Rickard | A61B 3/16 604/9 |
| 2013/0085440 A1 | * | 4/2013 | Bohm | A61F 9/00781 604/9 |
| 2013/0096483 A1 | * | 4/2013 | Dacquay | A61F 9/00781 604/9 |
| 2013/0144202 A1 | * | 6/2013 | Field | A61F 9/00781 604/9 |
| 2013/0150777 A1 | * | 6/2013 | Bohm | A61F 9/00781 604/9 |
| 2013/0204177 A1 | * | 8/2013 | Field | G06Q 30/02 604/9 |
| 2014/0177881 A1 | * | 6/2014 | Fanget | H04R 3/002 381/190 |

* cited by examiner

*Primary Examiner* — Paul Prebilic
(74) *Attorney, Agent, or Firm* — Haynes and Boone, LLP

(57) ABSTRACT

A valve system for an ocular implant device includes a boss structure. The boss structure includes an inlet for fluid inflow, and a number of outlets for fluid outflow. The valve system further includes a deformable membrane positioned over and spaced apart from the inlet, the membrane comprising a piezo-based material, an actuating element to apply pressure to the membrane to deform the membrane into a position that obstructs fluid flow from the inlet, and a control system to detect a position of the membrane based on measured electrical properties of the membrane.

20 Claims, 5 Drawing Sheets

VALVE POSITION DETECTION

FIELD OF THE INVENTION

The present disclosure relates to apparatuses and methods incorporating a valve position detection system, and more particularly, to apparatuses and methods including the position detection system in an implantable device.

BACKGROUND

Glaucoma, a group of eye diseases affecting the retina and optic nerve, is one of the leading causes of blindness worldwide. Most forms of glaucoma result when the intraocular pressure (IOP) increases to pressures above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision.

FIG. 1 is a diagram of the front portion of an eye that helps to explain the processes of glaucoma. In FIG. 1, representations of the lens 110, cornea 120, iris 130, ciliary body 140, trabecular meshwork 150, and Schlemm's canal 160 are pictured. Anatomically, the anterior segment of the eye includes the structures that cause elevated IOP which may lead to glaucoma.

Aqueous humor fluid is produced by the ciliary body 140 that lies beneath the iris 130 and adjacent to the lens 110 in the anterior segment of the eye. This aqueous humor washes over the lens 110 and iris 130 and flows to the drainage system located in the angle of the anterior chamber. The angle of the anterior chamber, which extends circumferentially around the eye, contains structures that allow the aqueous humor to drain.

The trabecular meshwork 150 is commonly implicated in glaucoma. The trabecular meshwork 150 extends circumferentially around the anterior chamber. The trabecular meshwork 150 seems to act as a filter, limiting the outflow of aqueous humor and providing a back pressure that directly relates to IOP.

Schlemm's canal 160 is located beyond the trabecular meshwork 150. The Schlemm's canal 160 is fluidically coupled to collector channels (not shown) allowing aqueous humor to flow out of the anterior chamber. The two arrows in the anterior segment of FIG. 1 show the flow of aqueous humor from the ciliary bodies 140, over the lens 110, over the iris 130, through the trabecular meshwork 150, and into the Schlemm's canal 160 and its collector channels.

One method of treating glaucoma includes implanting a drainage device in a patient's eye. The drainage device allows fluid to flow from the interior chamber of the eye to a drainage site, relieving pressure in the eye and thus lowering IOP. In some cases, a valve is used to control the flow through the drainage device.

In order to provide consistency and accuracy in fluid flow through the drainage device, it may be important to limit changes and degradation that may occur in the drainage device over time. To do this, it may be important to know the position of the valve such as the amount or percentage that the valve is open or closed at a given moment in time. The system and methods disclosed herein overcome one or more of the deficiencies of the prior art.

SUMMARY

This disclosure relates generally to, and encompasses, apparatuses and methods for removing ocular tissue and/or fluid from the eye, and more specifically to ophthalmic surgical systems and methods of using the systems to remove ocular tissue and/or fluid from the eye.

According to some embodiments, a valve system for an ocular implant device includes a boss structure. The boss structure includes an inlet for fluid inflow, and a number of outlets for fluid outflow. The valve system further includes a deformable membrane positioned over and spaced apart from the inlet, the membrane comprising a piezo-based material, an actuating element to apply pressure to the membrane to deform the membrane into a position that obstructs fluid flow from the inlet, and a control system to detect a position of the membrane based on measured electrical properties of the membrane.

According to some embodiments, a valve system for an ocular implant device includes a boss structure. The boss structure includes an inlet for fluid inflow, and a number of outlets for fluid outflow. The valve system further includes a deformable membrane positioned over and spaced apart from the inlet. The membrane includes a support layer and a piezo-resistive layer. The valve system further includes an actuating element to apply pressure to the membrane to adjust a position of the membrane to adjust fluid flow between the inlet and the outlets, a sensor to detect an electrical characteristic of the membrane, and a control system to determine the position of the membrane based on a measured electrical property of the membrane.

According to some embodiments, a method for determining a position of a valve in an ocular implant includes applying a voltage to a piezoresistive membrane, the membrane being deformable between an open position, that allows fluid flow between an inlet and a number of outlets, and a closed position that obstructs flow between the inlet and the outlets. The method further includes measuring an electric current flowing through the membrane to determine a measured electric current value, and determining a position of the membrane based on the measured electric current value.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
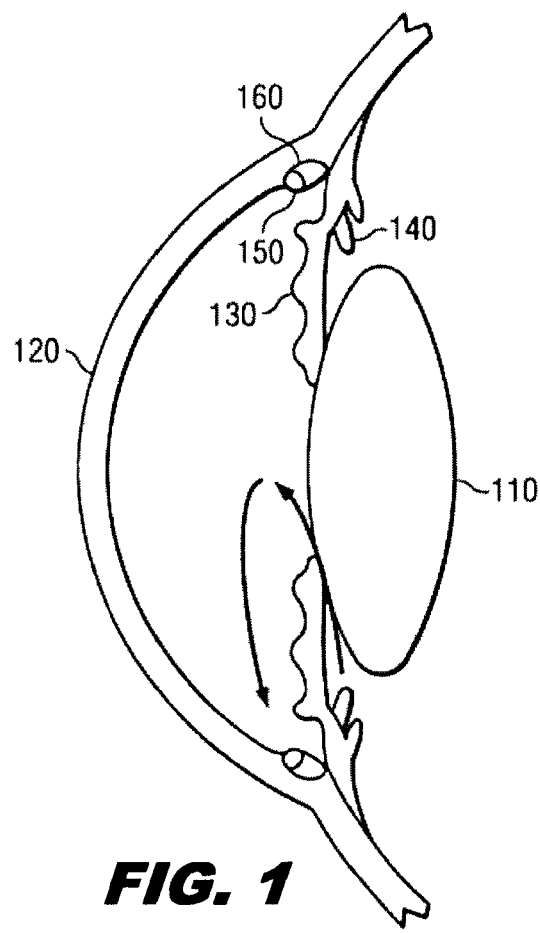
FIG. 1 is a diagram of the front portion of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

This disclosure is directed to devices, systems, and methods that determine the position, as an amount or degree to which the valve is open or closed. The exemplary aspects described herein include a membrane valve can be used to control the flow of aqueous humor through a drainage device implant. Because the membrane valve is very small, it can be difficult to determine the actual position of the membrane valve. In addition, damage can occur if too much pressure is applied to the membrane valve. By knowing the position of the membrane valve, a control system can determine how much pressure should be applied to move the membrane to the desired position.

According to certain embodiments, the devices, systems, and methods described herein monitor electrical characteristics of the valve to determine its position. In some aspects, the membrane valve includes at least one layer that is made of a piezo-based material, such as a piezoresistive material or a piezoelectric material. Piezo-based materials exhibit specific electrical characteristics that have a direct relationship with applied mechanical forces.

For example, a piezoresistive material changes its resistance in a predictable manner based upon its shape. By applying a voltage to the membrane, and then measuring the electric current flowing through the membrane, the resistance of the piezoresistive membrane can be determined. By knowing the resistance, the position of the membrane can be determined.

In the case of a piezoelectric material, electric current is produced during movement of the membrane. This current can be measured and correlated with a change in position of the membrane. By knowing a starting position and a change in position of the membrane, it is possible to determine the present position of the membrane.

Figure 2:
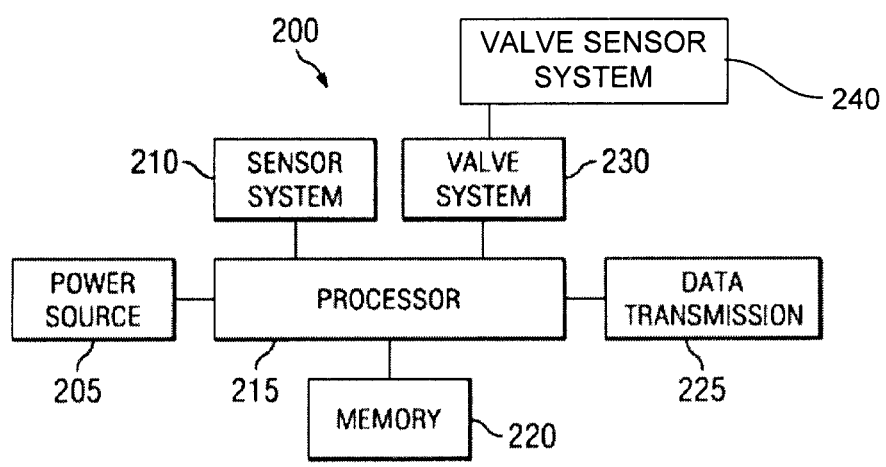
FIG. 2 is a block diagram of an exemplary IOP control system according to one example incorporating the principles described herein.

FIG. 2 is a block diagram of an exemplary IOP control system 200 implantable in an eye of a patient for the treatment of glaucoma or other conditions. The IOP control system 200 is configured in a manner that provides IOP pressure control, but also regulates and controls bleb pressures, reducing complications arising from surgical implant glaucoma treatments. In FIG. 2, the IOP control system 200 includes a power source 205, an IOP sensor system 210, a processor 215, a memory 220, a data transmission module 225, a valve system 230, and a valve sensor system 240.

The power source 205, which provides power to the IOP control system 200, is typically a rechargeable battery, such as a lithium ion or lithium polymer battery, although other types of batteries may be employed. The power source can be recharged via inductive coupling such as an RFID link or other type of magnetic coupling.

The processor 215 is typically an integrated circuit with power, input, and output pins capable of performing logic functions. In various embodiments, the processor 215 may be a targeted device controller or a microprocessor configured to control more than one component of the device.

The memory 220, which is typically a semiconductor memory such as RAM, FRAM, or flash memory, interfaces with the processor 215. As such, the processor 215 can write to and read from the memory 220, and perform other common functions associated with managing semiconductor memory. In this manner, a series of IOP readings can be stored in the memory 220.

The data transmission module 225 may employ any of a number of different types of data transmission. For example, in various embodiments, the data transmission module 225 may be an active device such as a radio or a passive device with an antenna on an RFID tag. Alternatively, the data transmission module 225 may be activated to communicate an elevated IOP condition to a secondary device such as a PDA, cell phone, computer, wrist watch, custom device exclusively for this purpose, remote accessible data storage site (e.g. an internet server, email server, text message server), or other electronic device or service.

The valve system 230 includes one or more valves, pumps or other flow regulators to pride at least some regulation of fluid flow through the IOP control system 200. In the embodiments described herein, and as described further below with reference to FIGS. 4A, 4B, 5, and 6, the valve system 230 may include a membrane valve with a flexible membrane that is displaceable to regulate flow through the membrane valve.

The valve sensor system 240 may form a part of the valve system and may measure the electrical properties of the membrane valve. For example, the valve sensor system 240 includes a voltage supply to apply an excitation voltage to the membrane. The valve sensor system 240 also includes an electric current measuring device such as an ammeter to measure the electric current flowing through the membrane. Additionally, the valve sensor system 240 may include various pressure sensors that are used to determine how much fluid flow should be allowed through the valve system 230.

Figure 3:
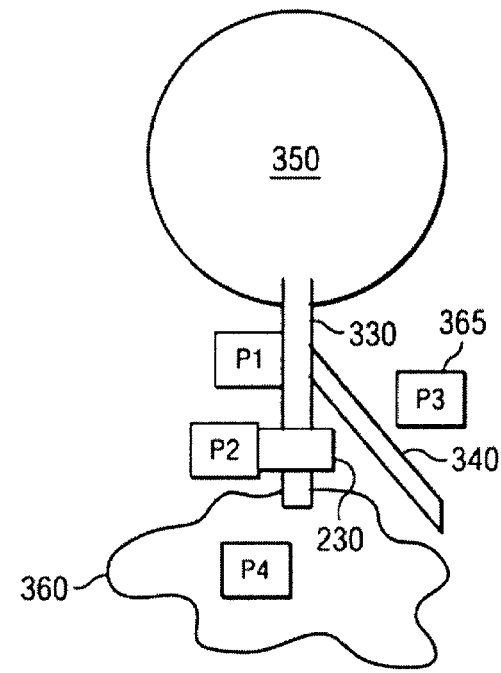
FIG. 3 is a schematic diagram of an exemplary IOP control system according to one example incorporating the principles described herein.

FIG. 3 is a diagram of at least a portion of the IOP control system 200 disposed along elements of an eye. Here, the IOP control system 200 includes the exemplary IOP sensor system 210, a drainage tube 330, the valve system 230, and a divider 340. In FIG. 3, the IOP sensor system 210 includes four pressure sensors, P1, P2, P3, and P4. The pressure sensor P1 is located in or is in fluidic communication with an anterior chamber 350 of an eye, the pressure sensor P2 is located to measure intermediate pressures found within the valve system 230, the pressure sensor P3 is located remotely from P1 and P2 in manner to measure atmospheric pressure, and the pressure sensor P4 is located at a drainage site 360 in the subconjunctival space and is arranged to measure bleb pressure.

In some embodiments, the pressure sensor P1 is located in a lumen or tube that is in fluid communication with the anterior chamber of an eye. The pressure sensor P4 may be located in a pocket, such as a bleb, that generally contains aqueous humor or in communication with such a pocket, via a tube for example, and is in the wet site 360. The drainage site 360 may be, by way of non-limiting example, in a subconjunctival space, a suprachoroidal space, a subscleral space, a supraciliary space, Schlemm's canal, a collector channel, an episcleral vein, and a uveo-scleral pathway, among other locations in the eye.

The drainage tube 330 drains aqueous humor from the anterior chamber 350 of the eye. The valve system 230 controls the flow of aqueous humor through the tube 330. In the embodiment shown, the pressure sensor P1 measures the pressure in the tube 330 upstream from the valve system 230 and downstream from the anterior chamber 350. In this manner, pressure sensor P1 measures the pressure in the anterior chamber 350. The expected measurement discrepancy between the true anterior chamber pressure and that measured by P1 when located in a tube downstream of the anterior chamber (even when located between the sclera and the conjunctiva) is very minimal. For example, Poiseuille's law for pipe flow predicts a pressure drop of 0.01 mmHg across a 5-millimeter long tube with a 0.300 millimeter inner diameter for a flow rate of 3 microliters per minute of water.

In some embodiments, the system includes barriers that separate the sensors P1, P2, P3, and P4. These barriers may be elements of the system itself. For example, in FIG. 3, the pressure sensor P3 is physically separated from the pressure sensor P4 by the divider 340. The divider 340 is a physical structure that separates the wet site 360 of P4 from the dry site 365 of P3. In one example, the barrier separating the anterior chamber pressure sensor P1 and the drainage site pressure sensor P4 is the valve system 230.

Generally, IOP is a gauge pressure reading—the difference between the absolute pressure in the eye (as measured by P1) and atmospheric pressure (as measured by P3). In one embodiment of the present disclosure, pressure readings are taken by the pressure sensors P1 and P3 simultaneously or nearly simultaneously over time so that the actual IOP can be calculated (as P1−P3 or P1−f(P3), where f(P3) indicates a function of P3). The pressure readings of P1 and P3 can be stored in memory 220 by the processor 215. They can later be read from memory so that actual IOP over time can be interpreted by a physician.

The pressure sensors P1, P2, P3, and P4 can be any type of pressure sensors suitable for implantation in the eye. They each may be the same type of pressure sensor, or they may be different types of pressure sensors.

Since the pressure sensor P1 measures the pressure in the anterior chamber 350 and pressure sensor P4 measures pressure at the drainage site 360, the difference between the readings taken by these two pressure sensors (P1−P4) provides an indication of the pressure differential between the anterior chamber 350 and the drainage site 360. In one embodiment, this pressure differential dictates the rate of aqueous humor flow from the anterior chamber 350 to the drainage site 360.

Readings from the pressure sensors P1, P2, P3, and P4 can be used to control the flow rate through the tube 330 by controlling the valve system 230. For example, the valve system 230 may be controlled based on the pressure readings from pressure sensors P1, P2, P3, and P4. The valve system 230 may be controlled by the processor 215 based on input data received from the sensors. A desired pressure differential (that corresponds to a desired flow rate) can be maintained by controlling the operation of the valve system 230. Likewise, various intraocular pressure parameters, such as, by way of non-limiting example, the desired IOP, the IOP change rate, and/or the bleb pressure may be controlled by controlling the operation of valve system 230. Note that in some embodiments, the physician is able to set the high/low IOP thresholds wirelessly to meet each patient's specific requirements.

Figure 4A:
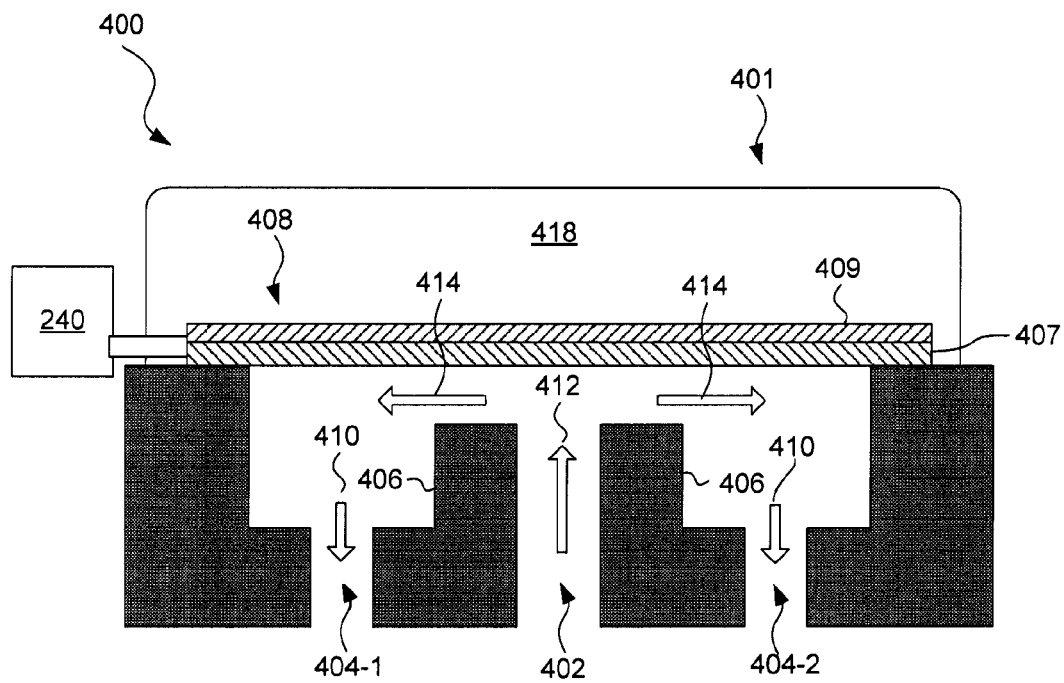
FIGS. 4A and 4B are diagrams showing a piezo-based membrane valve in an open and closed position according to one example incorporating the principles described herein.
Figure 4B:
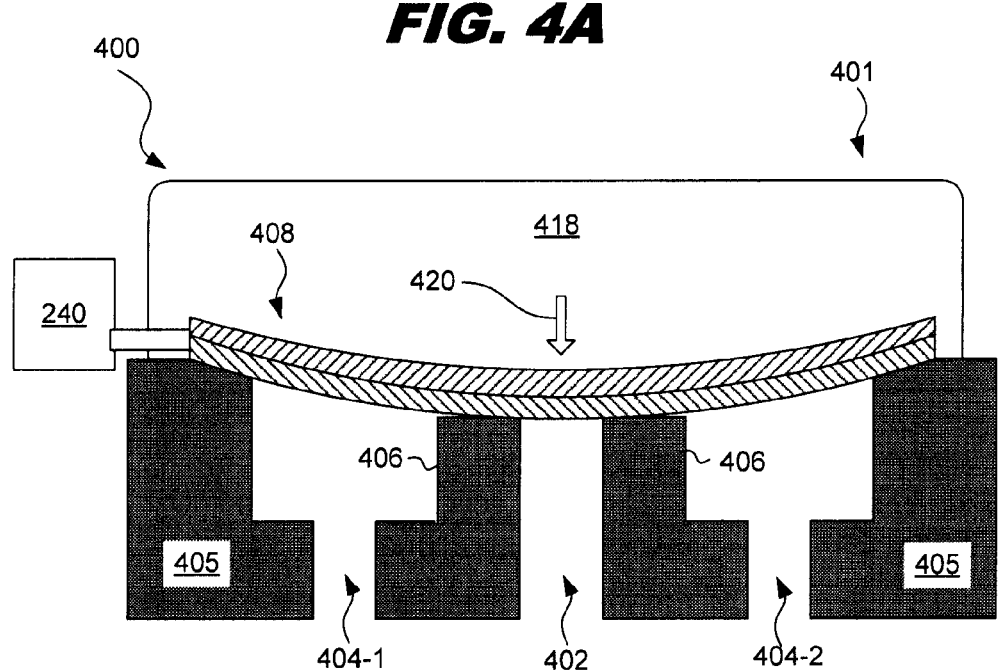

FIGS. 4A and 4B are diagrams showing a valve system 400 with a piezo-based membrane valve 401 in an open and in a closed position, respectively. The valve system 400 may be part of the valve system 230 described above. FIG. 4A illustrates a stylized cross-sectional view of the membrane valve 401 in the open position. According to the exemplary embodiment, the valve system 400 includes a housing 405 and a boss structure 406 having an inlet 402 extending therethrough. The valve system 400 also includes a number of outlets 404, a membrane 408, an actuating element 418, and a valve sensor system 230.

The fluid inlet 402 is in fluid communication with the anterior chamber (e.g. 350, FIG. 3) of the patient's eye. The inlet 402 is positioned in the center of the boss structure 406.

The boss structure 406 is a support structure through which fluid flows. The boss structure 406 supports the fluid inlet 402. In one example, the boss 406 structure may be circular from a top perspective. In some embodiments, the boss structure 406 may be elliptical, or rectangular from the top perspective. Other shapes for the boss structure are contemplated.

The outlets 404 lead, directly or indirectly, to a drainage site (e.g. 360, FIG. 3). The outlets are formed into a housing 405. In the illustrated embodiment, the outlets 404-1, 404-2 are positioned at opposite sides from each other. Thus, the inlet 402 is positioned between the two different outlets 404-1, 404-2. While only two outlets 404 are shown, in some embodiments, there may be one or more additional outlets 404. For example, one exemplary embodiment includes five outlets 404 forming a circle around the inlet 402, when viewed from the top perspective.

The membrane 408 is a thin layer of material that is flexible and can thus be displaced under pressure. The membrane 408 may be supported at the edges by the housing 405. The membrane 408 is disposed to extend across the boss structure 406, the opening of the inlet 402, and the openings of the outlets 404. The membrane 408 is configured to deflect toward and away from the interfacing surface of the boss structure 406 to inhibit or regulate flow from the inlet in varying degrees.

In some embodiments, the membrane 408 may include multiple layers. In the illustrated embodiment, the membrane 408 includes a support layer 407, and a piezo-based layer 409. In some examples, the support layer 407 may be made of a thin piece of glass or silica. In some examples, the support layer 407 may be formed of a biocompatible elastomeric material such as, by way of non-limiting example, Parylene, silicone, silicone nitride, silicone elastomeric, and polyimide.

The piezo-based layer 409 may be made of a variety of materials. For example, the piezo-based layer 409 may be a thin film grown through an epitaxial process. The thin film may be a semiconductor material such as silicon and may be doped with a variety of dopants including boron, arsenic, aluminum nitride, zinc oxide, lead zirconate titanate and/or others. In some examples, the piezo-based layer 409 may be a ceramic metal compound such as a combination of silicon oxide and chromium grown over a thin membrane, or coated by, a crystalline substrate such as sapphire. In some embodiments, a piezoresistive layer may be made of polysilicon or other type of semiconductor material. Other piezo-based materials are contemplated.

The actuating element 418 applies pressure to the membrane 408 to cause deflection of the membrane to or away from the boss structure 406 and inlet 402. The actuating element 418 may be formed of any variety of mechanisms to actuate the membrane 408. In one example, the actuating element 418 may utilize electrolysis to apply pressure to the membrane 408. Particularly, the actuating element 418 may include a chamber containing electrodes. The chamber may be filled with an electrolytic fluid. Some of the electrolytic fluid will change from a liquid state to a gas state under application of a voltage by the electrodes. This will cause a pressure build up in the chamber, thereby pressing against the membrane 408. Other methods of actuation are also contemplated.

The valve sensor system 240 includes the tools used to measure the electrical properties of the membrane 408. The valve sensor system 240 may be part of the control system 200 illustrated in FIG. 2. The valve sensor system 240 includes a voltage supply to apply an excitation voltage to the membrane 408. The control system 416 also includes an electric current measuring device such as an ammeter to measure the electric current flowing through the membrane 408.

When in an open position, the valve system 400 allows fluid flow 412 through the inlet 402 toward the membrane 408. The valve system 400 also allows fluid flow 414 between the inlet and the outlets 404. The fluid flow 410 then continues through the outlets 404 to the drainage site. During normal operation, the 10P control system 200 of a device implant utilizing the valve system 400 may determine that the pressure in the anterior chamber is too low. Thus, the valve system 400 should be closed so that fluid no longer flows from the anterior chamber to the drainage site.

FIG. 4B illustrates the valve system 400 in a closed position. According to one embodiment, pressure 420 applied to the membrane 408 increases the deflection of the membrane 408. The pressure 420 can be controlled to press the membrane 408 against the opening of the inlet 402 with enough force to prevent fluid flow 412 through the inlet 402.

Being aware of the position of the membrane 408 may be important when determining how much pressure 420 should be applied to regulate or block fluid flow through the valve structure. Specifically, if the membrane 408 is already pressed against the boss structure 406, then applying additional pressure may cause damage.

Figure 5:
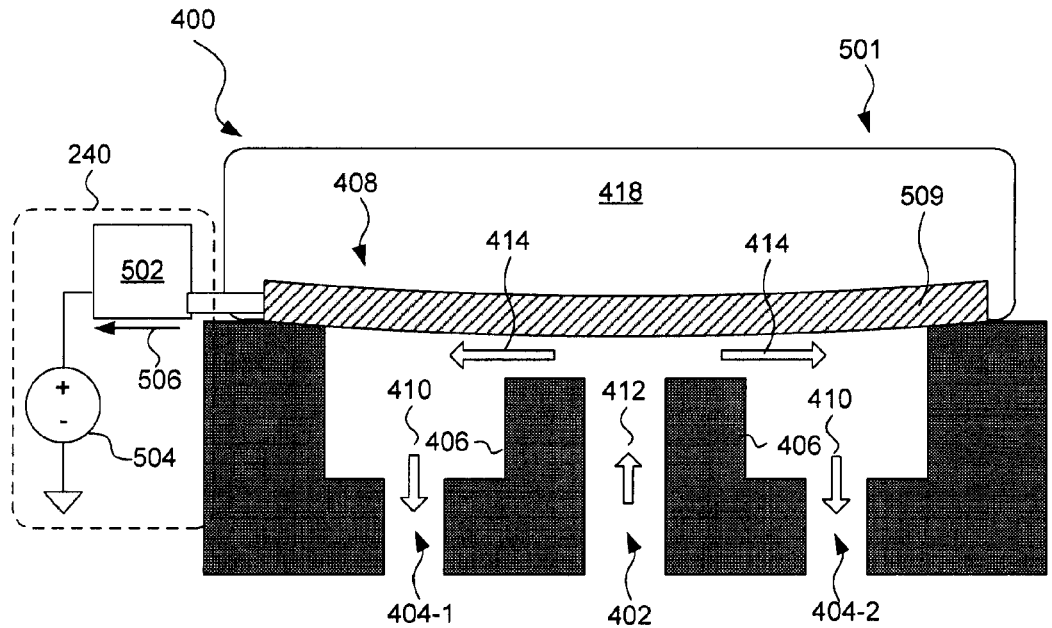
FIG. 5 is a diagram showing a piezoresistive membrane valve according to one example incorporating the principles described herein.

FIG. 5 is a diagram showing a valve system 400 with a piezoresistive membrane valve 501. The piezoresistive membrane valve 501 may form part of the valve system 400 described above with references to FIGS. 2 and 3. Some of the features of the piezoresistive membrane valve 501 are the same as the features of the piezo-based membrane valve 401. Accordingly, not all the features will be discussed again as the above description applies. Like the pizezo-based membrane valve 401 discussed above, the piezoresistive membrane valve 501 includes a membrane 408 and a control system 240. In this embodiment, however, the membrane 408 comprises a layer of a piezoresistive material 509. A piezoresistive material 509 is a material that changes its electrical resistance based on mechanical stress. Thus, the resistance of the membrane 408 is a function of the deflection position of the membrane 408.

The control system 240 includes a voltage supply 504 and a current measuring device such as an ammeter 502. The voltage supply 504 applies a small voltage to the membrane 408. This will cause a current 506 to flow through the membrane 408. The electric current 506 passing through the membrane is then measured by the ammeter 502. The resistance can then be calculated based on the applied voltage and the measured current 506. Specifically, the resistance is equal to the voltage divided by the measured current. The resistance can then be used to determine the deflection position of the membrane 408.

The position of the membrane 408 in FIG. 5 may be determined based on the resistance in a number of manners. In one example, before use of the valve system, the resistance of the membrane 408 at a set of known positions is measured. For example, the resistance of the membrane 408 may be measured at 10 different points between fully open and fully closed positions. This set of data may be used to determine the position of the membrane during normal operation. Particularly, if the determined resistance is a value close to a value corresponding to one of the points that was previously measured, then it is known that the present position of the membrane 408 corresponds to that position.

In some embodiments, a function can be used to determine the position of the membrane 408 based on its resistance. This function may be extracted from a set of data points as described above. Or, the function may be derived based on known piezoresistive and mechanical properties of the membrane. Thus, to determine the position of the membrane 408, the valve sensor system 240 in FIG. 5 may plug in the calculated resistance value into the function to determine the position of the membrane 408.

Figure 6:
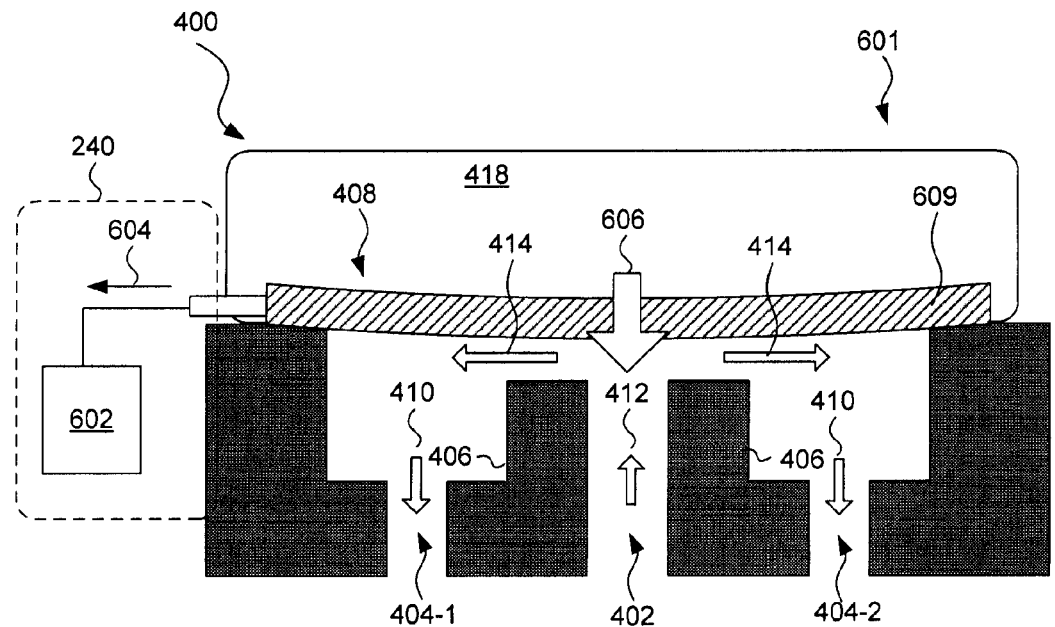
FIG. 6 is a diagram showing a piezoelectric membrane valve according to one example incorporating the principles described herein.

FIG. 6 is a diagram showing a piezoelectric membrane valve 601. Again, some of the features of the piezoelectric membrane valve 601 are the same as the features of the piezo-based membrane valve 401. Accordingly, not all the features will be discussed again as the above description applies. Like the piezo-based membrane valve 401 discussed above, the piezoelectric membrane valve 601 includes a membrane 408 and a control system 240. In this embodiment, however, the membrane 408 comprises a layer of a piezoelectric material 609. A piezoelectric material 609 will generate an electric current while moving from one position to another. Thus, the present position of the piezoelectric membrane 408 is a function of a previously known position and a current measurement taken during movement between the present position and the previous position.

The valve sensor system 240 for the piezoelectric membrane 408 includes a current measuring device such as an ammeter 602. The ammeter 602 measures an electric current 604 flowing from the membrane 408 in response to a change in deflection position of the membrane 408.

The position of the membrane 408 may be determined based on the measured current in a number of manners. In one example, a function is derived that correlates electric current with change in position. This function is then used to determine the change in position based on a measured current value. By knowing the previous position and the change in position, it is possible to determine the current position. Other methods for determining the position based on the measured electric current are contemplated.

Figure 7:
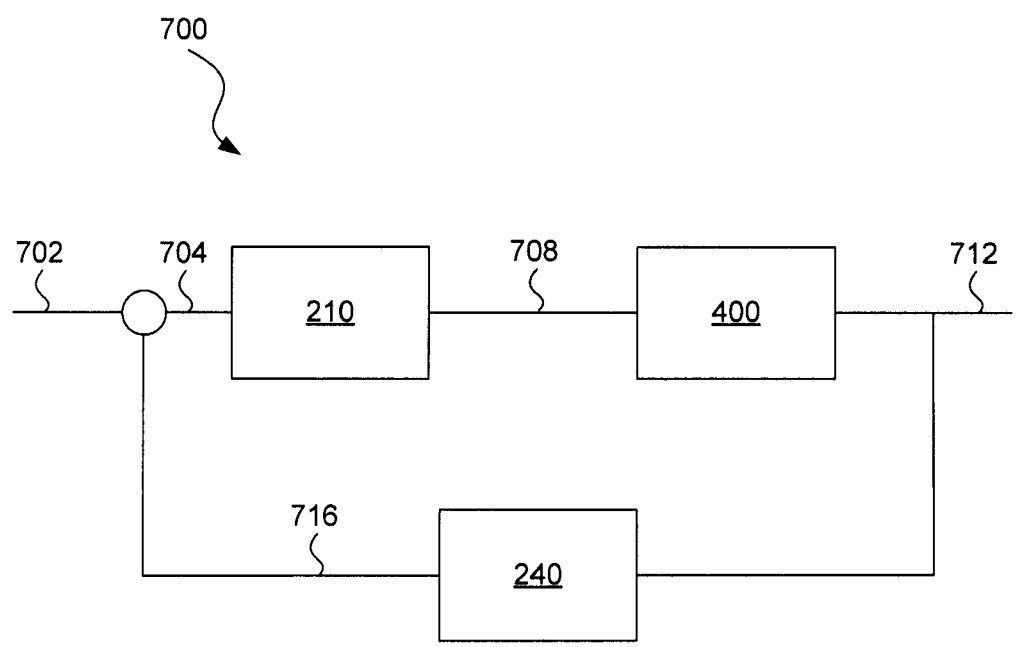
FIG. 7 is a diagram showing an illustrative feedback control system for a membrane valve according to one example incorporating the principles described herein.

FIG. 7 is a diagram showing an illustrative feedback control system 700, which may form a part of the IOP control system 200. Feedback control systems can be used to achieve a desired output based on an input. For example, it may be desirable that the membrane (e.g. 408, FIG. 4) be at a specific position. The specific position may be either fully closed or fully open. The specific position may also be somewhere in between.

The feedback control system 700 includes an input 702, an error 704, the IOP sensor system 210, a system input 708, the valve system 400, an output 712, the valve sensor system, and a measured output 716. For convenience, the feedback control system 700 will be discussed with reference to the valve system 400, recognizing that it may be used with all valve systems described herein.

The operation of the feedback control system 700 will become more apparent in view of the following example. In one example, the valve is 20% closed and it is desired to move the valve to a position that is 80% closed. Thus, the input 702 of the system is set to 80% closed. At that time, the output 712 of the valve system 400 is still at 20% closed. The measured error 704 is the difference between the input 702 and the measured output 716. In this case, the measured error 704 is 60%. Thus, the 10P sensor system 210, which operates as the feedback controller in this case, knows to apply more pressure to the membrane to make the measured error 704 zero.

By using the methods and principles described herein, the measured output 716 more closely resembles the actual system output 712. Thus, the IOP sensor system 210 can more accurately adjust the valve system 400 to the desired position. Moreover, the IOP sensor system 210 will regulate pressure on the membrane when the membrane is already in the fully closed position to avoid over-pressurization conditions that may cause damage to the membrane.

Figure 8A:
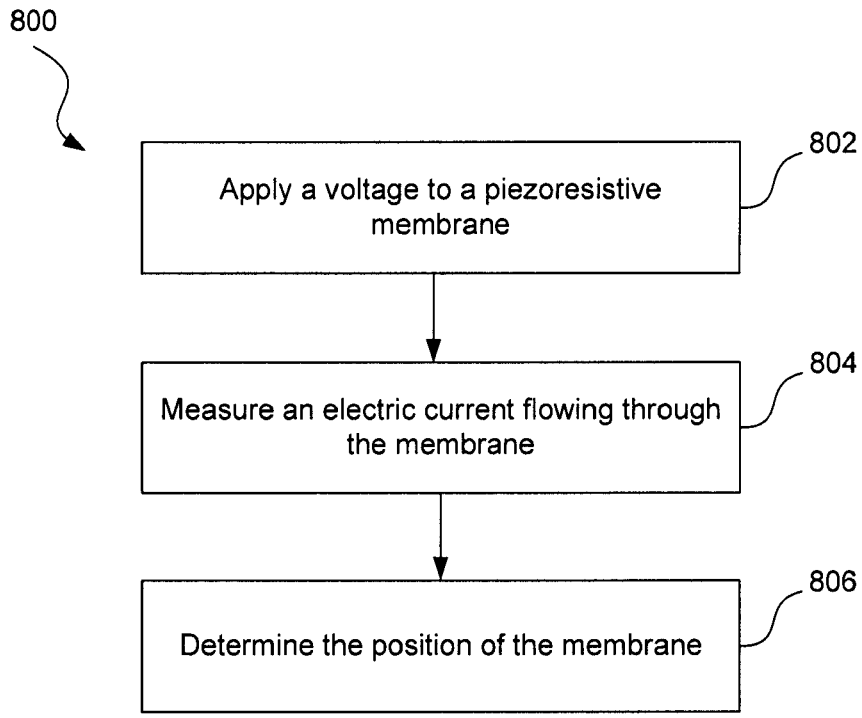
FIGS. 8A and 8B are flowcharts illustrating methods for determining the position of a piezo-based membrane valve according to examples incorporating the principles described herein.
Figure 8B:
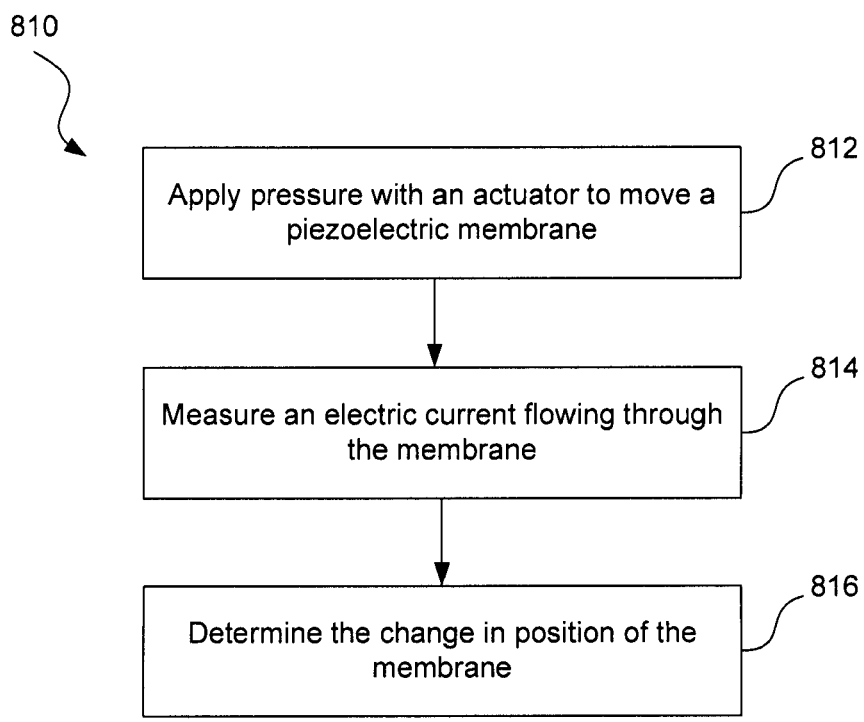

FIGS. 8A and 8B are flowcharts illustrating methods for determining the position of a piezo-based membrane valve. FIG. 8A is a flowchart showing an illustrative method for determining the position of a piezoresistive membrane valve, while FIG. 8B describes a method for determining the position of piezoelectric membrane valve. Referring first to FIG. 8A, and according to the present example, the method 800 includes applying a voltage to a piezoresistive membrane at step 802. This voltage will cause an electric current to flow through the piezoresistive membrane.

The method 800 further includes measuring an electric current flowing through the membrane at step 804. This may be done with a current measuring device such as an ammeter. Resistance is equal to the voltage applied divided by the electric current flowing through the membrane. Thus, the resistance is determined by applying a known voltage and measuring the current.

The method further includes determining a position of the membrane at step 806. This is done based on the calculated resistance value. As described above, the position can be determined from the resistance based on either a predefined data set or by applying the resistance value to a function that relates resistance to valve position.

FIG. 8B illustrates a method 810 for determining the position of a membrane valve made of a piezoelectric material. According to one embodiment, the method 810 includes applying pressure with an actuating element to move a piezoelectric membrane at step 812. As described above, the actuating element may use electrolysis to move the membrane.

Because of the piezoelectric properties of the membrane, movement of the membrane will cause an electric current to flow through the membrane. The method 810 includes measuring an electric current flowing through the membrane at step 814. This may be done with a current measuring device such as an ammeter.

The method 810 includes determining a change in position of the membrane at step 816. The change in position is based off of the measured electrical current during the change. As described above, this may be done using a predefined data set or a function that relates measured current during change to the change in position. Knowing the original position and the change in position of the membrane allows for determination of the present position of the membrane.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

We claim:

1. A valve system for an ocular implant device, the valve system comprising:
   a housing;
   a boss structure connected to the housing, the boss structure comprising an inlet for fluid inflow;
   a number of outlets within the housing, the outlets for fluid outflow;
   a displaceable membrane positioned over and spaced apart from the inlet, the membrane comprising a piezo-based material;
   an actuating element to displace the membrane into a position that obstructs fluid flow from the inlet;
   a control system to detect a position of the membrane based on measured electrical properties of the membrane.

2. The device of claim 1, wherein the piezo-based material comprises a piezoelectric material.

3. The device of claim 1, wherein the control system detects the position by measuring electric current flow during movement of the membrane.

4. The device of claim 1, wherein the piezo-based material comprises a piezoresistive material.

5. The device of claim 4, wherein the control system detects the position of the membrane by applying a voltage to the membrane and measuring current flowing through the membrane.

6. The device of claim 1, wherein the membrane comprises an epitaxial grown semiconductor material.

7. The device of claim 1, wherein the membrane comprises a semiconductor material doped with at least one of: boron, aluminum nitride, zinc oxide, lead zirconate titanate, silicon oxide, and chromium.

8. The device of claim 1, wherein the control system uses a feedback control loop that uses a determined position of the membrane to move the membrane to a desired position.

9. The device of claim 1, wherein the control system uses a feedback control system to control the actuating element and adjust fluid flow between the inlet and the outlets.

10. The device of claim 1, wherein the actuating element utilizes electrolysis to apply pressure to the membrane.

11. A valve system for an ocular implant device, the valve system comprising:
    a boss structure comprising:
    an inlet for fluid inflow;
    a number of outlets for fluid outflow; and a displaceable membrane positioned over and spaced apart from the inlet, the membrane comprising:
a piezo-resistive layer;
an actuating element to adjust a position of the membrane to adjust fluid flow between the inlet and the outlets;
a sensor to detect an electrical characteristic of the membrane; and
a control system to determine the position of the membrane based on a measured electrical property of the membrane.

12. The device of claim 11, wherein the sensor comprises:
a voltage supply to apply an excitation voltage to the membrane; and
a current measuring device to measure an electric current flowing through the membrane.

13. The device of claim 11, wherein the control system comprises:
a processor; and
a memory comprising machine readable instructions, that when executed by the processor, cause the processor to:
store a set of data comparing electrical resistance through the membrane to position of the membrane;
make a comparison between a measured value and the data; and
output a corresponding position value based on the comparison.

14. The device of claim 11, wherein the actuating element is configured to stop applying pressure when the membrane gets to a predetermined position.

15. The device of claim 11, wherein the actuating element is configured to change application of pressure in respond to the control system determining that the membrane is not in an intended position.

16. A system for determining a position of a valve in an ocular implant, the system comprising:
a voltage supply in electrical connection with a piezoresistive membrane, the membrane being deformable between an open position that allows fluid flow between an inlet and a number of outlets, and a closed position that obstructs flow between the inlet and the outlets;
an electric current sensor in connection with the piezoresistive membrane, the electric current sensor configured to measure an electric current flowing through the membrane as a result of a voltage applied by the voltage supply to the membrane; and
a control system to determine a position of the membrane based on a measured electric current value and the voltage applied by the voltage supply.

17. The system of claim 16, wherein to determine the position of the membrane, the control system is configured to:
compare the measured electric current with a set of data that correlates electric current values to positions of the piezoresistive membrane; and
output a position value that corresponds to the measured electric current.

18. The system of claim 16, wherein to determine the position of the membrane the control system is configured to apply a function to the measured electric current, the function relating electric current to position of the membrane.

19. The system of claim 16, further comprising, an actuating element configured to change its position at the piezoresistive membrane.

20. The system of claim 16, wherein the control system is further configured to:
at a repeating time interval, determine a position of the membrane; and
adjust the position of the membrane if the membrane is not in a desired position.

* * * * *